US010875056B2

(12) United States Patent
    Nijland (10) Patent No.: US 10,875,056 B2
(45) Date of Patent: Dec. 29, 2020

(54) MEASURING DEVICE FOR MEASURING PRODUCTS, AND METHOD THEREFOR

(71) Applicant: DE GREEF'S WAGEN-, CARROSSERIE-EN MACHINEBOUW B.V, Tricht (NL)

(72) Inventor: Wilhelm Jan Nijland, Veenendaal (NL)

(73) Assignee: De Greef's Wagen-, Carrossie- en Machinebouw B.V., Tricht (NL)

( * ) Notice: Subject to any disclaimer, the term of this patent is extended or adjusted under 35 U.S.C. 154(b) by 103 days.

(21) Appl. No.: 16/313,400

(22) PCT Filed: Jun. 29, 2017

(86) PCT No.: PCT/NL2017/050432
    § 371 (c)(1),
    (2) Date: Dec. 26, 2018

(87) PCT Pub. No.: WO2018/004342
    PCT Pub. Date: Jan. 4, 2018

(65) Prior Publication Data
    US 2019/0217341 A1    Jul. 18, 2019

(30) Foreign Application Priority Data

Jun. 29, 2016    (NL) .................................... 2017071

(51) Int. Cl.
    *B65G 13/07*    (2006.01)
    *B07C 5/342*    (2006.01)
    (Continued)

(52) U.S. Cl.
    CPC ............... *B07C 5/342* (2013.01); *B07C 5/36* (2013.01); *B65G 13/07* (2013.01); *G01N 33/025* (2013.01);
    (Continued)

(58) Field of Classification Search
    CPC . B07C 5/342; B07C 5/3416; B07C 2501/009; G01N 33/025
    See application file for complete search history.

(56) References Cited

U.S. PATENT DOCUMENTS 4,279,346 A  *  7/1981  McClure ............... B07C 5/3416
                                                         209/582
6,853,447 B2 *  2/2005  Goetz ..................... B07C 5/342
                                                         356/237.1
(Continued)

FOREIGN PATENT DOCUMENTS

EP    2261643 A1    12/2010
GB    2042717 A  *  9/1980 ............... B07C 5/10
(Continued)

OTHER PUBLICATIONS

International Search Report and Written Opinion dated Sep. 20, 2017 in International Patent Application No. PCT/NL2017/050432, 7 pages.

*Primary Examiner* — Patrick H Mackey
(74) *Attorney, Agent, or Firm* — Shook, Hardy & Bacon L.L.P.

(57) ABSTRACT

The invention relates to a measuring device for measuring products, such as fruits including vegetables and fruit, sorting system provided therewith, and method therefor. The measuring device according to the invention comprises: —a frame provided with a number of movable fruit carriers on which or between which products can be placed for carrying and with which the products can be moved in a transport direction; and a sensor configured to perform a measurement or series of measurements on the products on or between the fruit carriers, wherein at least parts of the sensor are configured to enable the sensor to perform measurements over a measuring path, and wherein the measuring path is arranged at an angle to the transport direction so that a (Continued)

measurement can be performed over a distance over the product.

20 Claims, 5 Drawing Sheets

(51) Int. Cl.
    *B07C 5/36*     (2006.01)
    *G01N 33/02*     (2006.01)

(52) U.S. Cl.
    CPC ............ *B07C 2501/009* (2013.01); *B65G 2201/0211* (2013.01); *B65G 2203/0258* (2013.01)

(56) References Cited

U.S. PATENT DOCUMENTS

| | | | | |
|---|---|---|---|---|
| 7,113,272 B2* | 9/2006 | Bourely | ............... | B07C 5/342 356/237.1 |
| 8,564,766 B2* | 10/2013 | Berghmans | ............ | B07C 5/342 356/237.3 |
| 8,746,435 B2* | 6/2014 | Nijland | ................. | B07C 5/18 198/370.04 |
| 10,083,496 B2* | 9/2018 | Peterson | ................ | G06T 3/40 |
| 2002/0079469 A1* | 6/2002 | Kennedy | ............... | B07C 5/342 250/559.4 |
| 2007/0229832 A1* | 10/2007 | Maeda | ................ | B07C 5/3416 356/419 |
| 2010/0290032 A1* | 11/2010 | Bugge | .................. | B07C 5/342 356/51 |
| 2016/0263624 A1* | 9/2016 | Balthasar | ............ | B07C 5/3416 |

FOREIGN PATENT DOCUMENTS

| | | |
|---|---|---|
| GB | 2042717 A | 9/1980 |
| WO | 8908510 A1 | 9/1989 |
| WO | 03023455 A1 | 3/2003 |

\* cited by examiner

MEASURING DEVICE FOR MEASURING PRODUCTS, AND METHOD THEREFOR

CROSS-REFERENCE TO RELATED APPLICATIONS

This application claims priority under 35 U.S.C. § 365 to PCT/NL2017/050432, filed on Jun. 29, 2017, entitled "MEASURING DEVICE FOR MEASURING PRODUCTS, AND METHOD THEREFOR," which claims priority to The Netherlands App. No. 2017071 filed on Jun. 29, 2016, the entirety of the aforementioned applications are incorporated by reference herein.

The present invention relates to a measuring device, particularly a measuring device for the purpose of sorting products, such as fruits in a general sense and more particularly vegetables and fruit.

Sorting devices are known in practice for sorting for instance vegetables and fruit. The products are herein measured and then classified according to a grouping into classes on the basis of the product measurement. The measurements are performed here on singulated products. The classified products are then transported to a sorting outlet of the sorting device and there collected along with other products in the same class for storage and/or further processing.

NL 1019600 describes a device for classifying products, wherein a product is irradiated with radiating means and wherein radiation receivers receive the resulting radiation. A feature of the product is measured on the basis of this received radiation. The product can then be grouped into a specific class, and thus be sorted, on the basis of this measurement. In a possible embodiment described in NL 1019600 the radiation receivers are disposed for reciprocal movement for the purpose of co-displacement thereof with the product holder. This extends the available measuring time.

A problem with conventional devices for measuring for the purpose of classifying products is that the dimensions of the products in question vary greatly. It is hereby difficult in practice to perform a measurement of good quality on products having such a great variation. This is for instance the case with pears, which usually have a clearly non-round form. The orientation of the product during the measurement therefore has a great influence on the finally obtained measurement result and the classification and sorting linked thereto. A good measurement in respect of the desired product feature is therefore not always obtained in the case of non-round and other products.

The present invention has for its object to provide a measuring device with which the above stated problems are obviated or at least reduced.

The present invention provides for this purpose a measuring device according to claim 1 for measuring products such as fruits, including vegetables and fruit.

By providing a measuring device with a number of fruit carriers on which or between which products can be carried, these products can be moved in a transport direction in relatively simple manner. During transport of the products in the measuring device the products are measured using a sensor. In a currently preferred embodiment this sensor is provided with a signal transmitter which is for instance arranged on the upper side of the fruit carriers at a fixed position, and one or more signal receivers which are arranged on the lower side of the fruit carriers. The transmitter is particularly suitable for transmitting infrared, visible light, UV radiation and/or X-radiation. It will be apparent that the radiation used depends on, among other factors, the type of product and the desired features of the product to be measured. It will be apparent that a different configuration of transmitters and receivers for the sensor according to the invention is also possible, for instance providing the transmitter on the lower side of the fruit carriers and receivers on the upper side thereof.

According to the invention, the sensor is able to perform measurements over a measuring path. More particularly, this makes it possible to perform measurements over a distance along the product. In comparison, in conventional systems a single measurement at a specific location usually suffices. The reliability and accuracy of the measuring device is hereby increased.

According to the invention, the measuring path is further oriented at an angle to the transport direction, substantially parallel to the measuring path, such that a measurement over a distance over the product can be realized. A product is provided with a number of dimensions expressed as length×width×height or as length×diameter, subject to the product form. Arranging the measuring path at an angle to the transport direction enables a measurement to be performed over at least a part of the length of the product and over a part of the remaining dimensions of the product. This achieves that a better indication is obtained of the quality of the product, particularly of the measured product feature, since one or more measurements can be performed over a product distance.

The transmitter of the sensor can be embodied as a single transmitter. It is also possible to provide a plurality of transmitters, preferably arranged at the same angle to the transport direction as a recess in a shield.

At least one receiver of the sensor is preferably provided, and more preferably provided are a plurality of receivers which are preferably arranged over the measuring path at an angle to the transport direction, substantially parallel to the recess in the shield.

It is possible to provide a plurality of frequencies or wavelengths with a single transmitter, for instance by providing a single signal and/or providing a plurality of signals with a specific frequency or specific frequency spectrum successively in time. The one or more receivers are here tuned to the one or more transmitters. A signal with a frequency spectrum can additionally or alternatively be provided.

Product features for instance relate to wholly or partially internal product features, such as internal browning, glassiness, watercore, sugar content/brix, acidity, types of browning/rotting (rot, core rot, fungi, pocket browning, nitrogen discoloration), juiciness, internal colour in for instance tomatoes, lycopene content in for instance tomatoes, vitamin content, firmness, ripeness, starch, number of cotyledons in for instance beans or onions, wall thickness in for instance bell peppers, the presence of seeds in for instance mandarin oranges, bitter pit, internal colour in for instance mangos, the presence of cavities, the presence of split stones in for instance stone fruit. It will be apparent that it is also possible to measure other product features.

According to the invention, the angle between the length of the recess and the transport direction lies in the range of 5° to 90° to the transport direction, preferably in the range of 20° to 70°, more preferably in the range of 30° to 60° and most preferably in the range of 40° to 50°. It has been found that at such an angle in the range of 5° to 90°, preferably in the range of 30° to 60°, a sufficiently accurate and robust measurement can be realized in practice, wherein a product feature can be measured over a certain distance along the product.

Measuring at an angle to the transport direction over a certain distance over the product further achieves a certain independence from the actual orientation of the product on the measuring device. A flexible and robust measuring device is hereby obtained, with which it has been found possible in practice to perform sufficiently accurate product measurements in respect of one or more product features at a relatively great speed.

In an advantageous embodiment according to the invention the measuring device further comprises a shield arranged between the fruit carriers and at least parts of the sensor, wherein the shield is provided with an elongate recess substantially parallel to the measuring path, wherein the recess is configured for passage of a measuring signal.

According to an embodiment of the invention, a shield is arranged between the fruit carriers and at least parts of the sensor, for instance particularly between the fruit carriers and one or more receivers of the sensor, in order to obtain an accurate measurement. The shield is provided with a recess. The dimensions of the recess, particularly in width direction of the recess, are such that the signal transmitted by the transmitter of the sensor is passed to the one or more receivers after being carried through the product, while disruptive influences from the surrounding area are avoided as far as possible. The width of the recess is therefore limited, for instance to 1-5 cm, so that disruptive influences are countered. The length of the recess depends on, among other factors, the dimensions of the measuring device and dimensions of the products transported thereby.

Providing a recess at an angle to the transport direction is particularly advantageous in non-round products, for instance pears, which generally have a relatively large bulbous end. It will be apparent that the measuring signal obtained with the one or more receivers depends on, among other factors, the measuring location on the product.

In an advantageous preferred embodiment according to the present invention the measuring device further comprises a moving device configured to move the sensor or parts thereof.

Arranging the sensor, or at least parts thereof, on a moving device enables the sensor, or at least the relevant parts, to move. This movement is preferably coordinated with the movement of the product over the measuring device. In a currently preferred embodiment one or more receivers are provided for being moved using the moving device. This moving device makes it possible to move the receivers, preferably on the lower side of the recess in the shield, so that a product which is moved on the measuring device in a transport direction can thereby in a certain sense be followed during the movement. This makes more effective measuring time available and/or increases the transport speed of the products, which increases the capacity of the whole system.

Because the recess is provided at an angle to the transport direction, a measurement over a distance along the product, instead of a measurement at a single point, is also made possible during the movement. A measurement on or over a section of the product, which preferably extends partially in longitudinal direction of the product and partially in a different direction, is particularly performed during the movement. A robust and reliable measurement of the relevant product feature is hereby obtained.

The moving device preferably comprises a drive provided with an arm on which the sensor, or parts thereof, are arranged. In the currently preferred embodiment already stated above one or more receivers of the sensor are arranged on the arm which is moved by the drive, preferably in a manner coordinated with the movement of the product. The movement of the sensor, or parts thereof, is coordinated with the recess which is arranged in the shield. The sensor movement is here substantially parallel to the longitudinal direction of the recess.

In a preferred embodiment the shield is embodied as a type of shielding plate. The drive of the moving device is preferably provided with a motor which achieves that the arm with the sensor, or parts thereof, can move over the measuring path. In an advantageous embodiment use is made here of an encoder. After measuring the product, the arm is temporarily moved back to the desired starting position for measuring a subsequent product.

In a currently preferred embodiment the arm of the moving device is provided for rotation around a rotation axis. In this embodiment the drive enables a rotation of the arm, or arms, around this rotation axis. The sensor, or parts thereof, therefore likewise make a rotating movement. The rotation axis is preferably disposed substantially transversely relative to the longitudinal direction of the recess, such that a movement of the sensor, or particularly the receivers thereof, substantially parallel to the recess in the shield is obtained by a rotation around the rotation axis of the moving device. After the desired measurements have been performed, the drive rotates the sensor, or parts thereof, as it were back to the starting position so it returns to the desired position in time to be able to measure a subsequent product. As already stated above, in a possible embodiment use is made of an encoder, which is for instance added to the shaft of the device.

The drive is preferably provided with a compensator, wherein the compensator is configured to compensate the movement of the arm, particularly the rotating movement of the arm, such that a substantially linear movement of the sensor, or parts thereof, substantially parallel to the longitudinal direction of the recess can be realized while a measurement is being performed. The linear movement of the sensor here preferably runs synchronously with the transport system. It will be apparent that, due to the rotating movement around the rotation axis, the speed of movement of the sensor, or parts thereof, in a direction parallel to the longitudinal direction of the recess varies and is dependent on the positions of the rotation axis and said recess. By compensating the driving with the compensator, the rotation speed is adjusted such that the speed of the sensor, or parts thereof, is substantially constant as seen in longitudinal direction of the recess, such that the arm (i.e. pendulum arm) runs substantially synchronously with the fruit carriers and/or intermediate spaces therein. This enables a robust measurement. The compensator can be provided in different ways, for instance mechanically and in the form of software. A software-based compensator can for instance be provided which acts on the control of the drive, particularly on the basis of the position of the fruit carrier, which in a preferred embodiment is determined by a position encoder on the shaft of the system.

The measuring device preferably further comprises a controller which is operatively connected to the sensor and is configured to control a measurement on the basis of product detection, for instance the moving device and transmitter thereof. By providing a controller the measurement can be adapted to the actual presence of a product for measuring and/or the correct position of the product and/or fruit carrier. A product detector which generates a signal as soon as the product is present and the measurement must be started is for instance provided for this purpose. The controller then sends an activation signal or control signal to for instance the drive of the measuring device and/or the sensor.

In a possible embodiment the controller controls the sensor and the measuring device substantially always co-displaces with the transport of the fruits. It is also possible to have the sensor measure continuously and to determine the presence or absence of a product from the measurement data. In a possible embodiment the controller is also provided with the above discussed compensator.

The sensor is preferably able to receive, and preferably process, signals with different wavelengths or frequencies of, preferably, the electromagnetic radiation which is transmitted by the transmitter of the sensor. It is also possible to apply a physical hardness tester, a laser, a methane sensor, spectrometer, X-ray detector, photosensitive element and the like in addition or as alternative to for instance an ultrasonic sensor. This enables different product features to be measured.

The fruit carriers are preferably embodied as diabolos. Such diabolos have been found particularly suitable for transporting irregularly shaped products such as pears. It is otherwise also possible to apply the measuring device in combination with otherwise embodied fruit carriers, for instance brush rollers, cups, holders or clamping systems.

The invention further also relates to a sorting system provided with a measuring device as described above.

Such a sorting system provides the same effects and advantages as described for the measuring device. In addition to the measuring device, the sorting system preferably comprises a singulator and a sorting device with sorting outlets. A complete processing line is hereby obtained with which products can be supplied in bulk and, after being singulated, measured and classified, can be sorted for the purpose of further processing, including storage. By making use of a robust and relatively rapid measurement with a measuring device according to the invention herein, a high capacity can be achieved for such a processing line.

The invention further also relates to a method for measuring products, such as fruits including vegetables and fruit, comprising the steps of:
  providing a measuring device and/or sorting system as described above;
  arranging a number of products on or between the fruit carriers;
  activating the sensor; and
  measuring the product over a measuring path at an angle to the transport direction.

The method provides similar effects and advantages as described for the measuring device and/or sorting system.

In a currently preferred embodiment the method further comprises of moving the sensor or parts thereof at an angle to the transport direction.

Further advantages, features and details of the invention are elucidated on the basis of preferred embodiments thereof, wherein reference is made to the accompanying drawings, in which.

Figure 1:
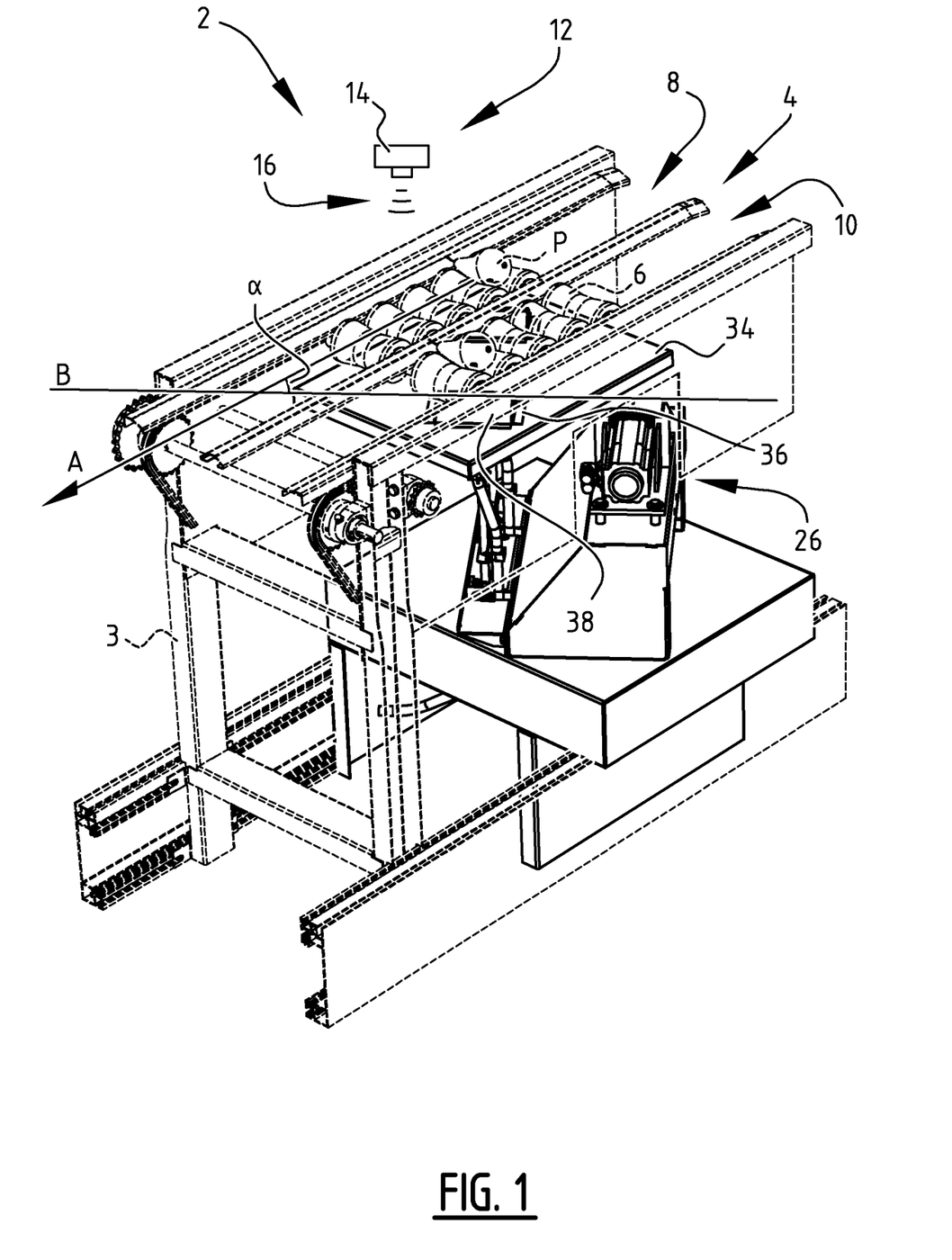
FIGS. 1-3 show different views of the measuring device according to the invention.
Figure 2:
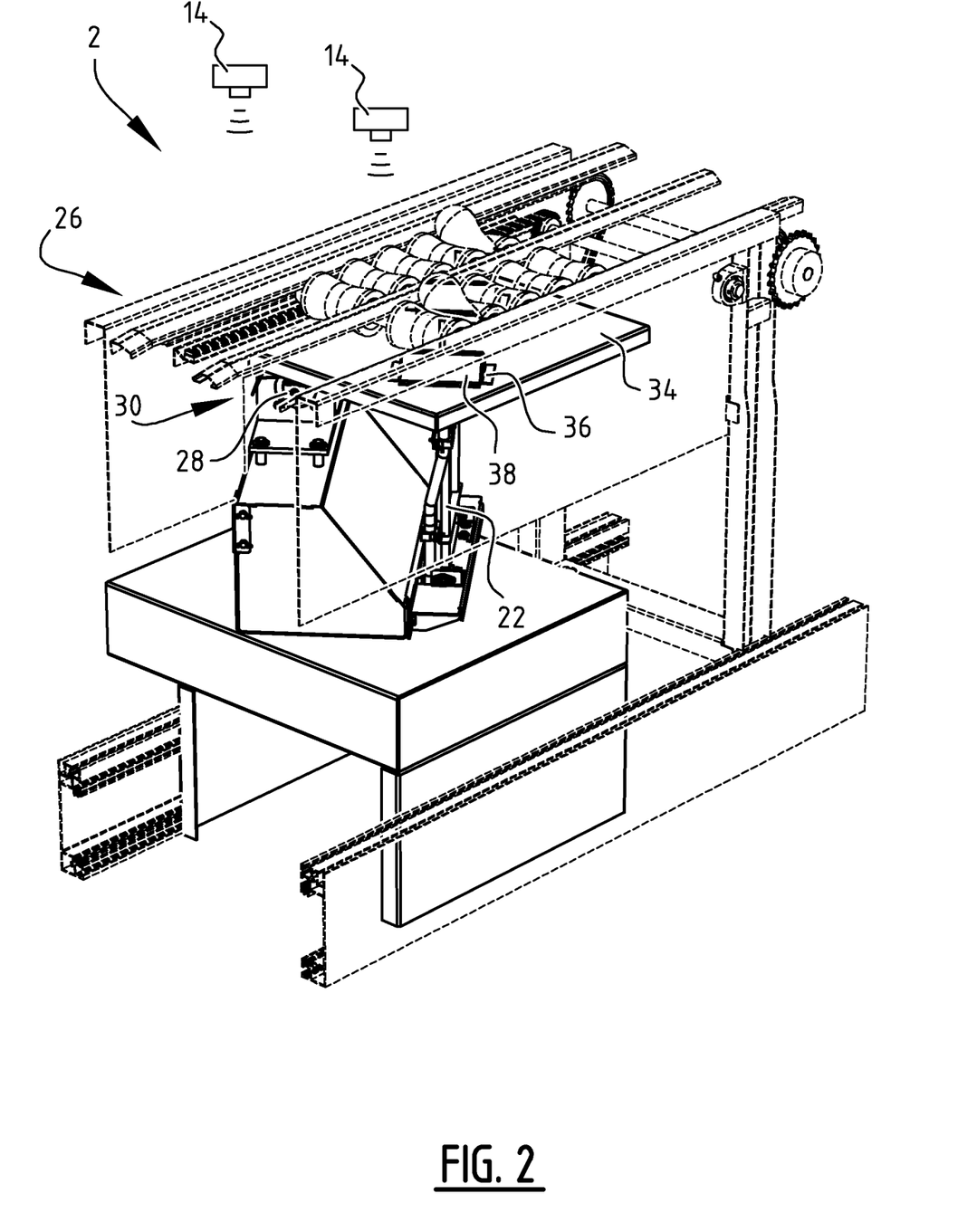
Figure 3:
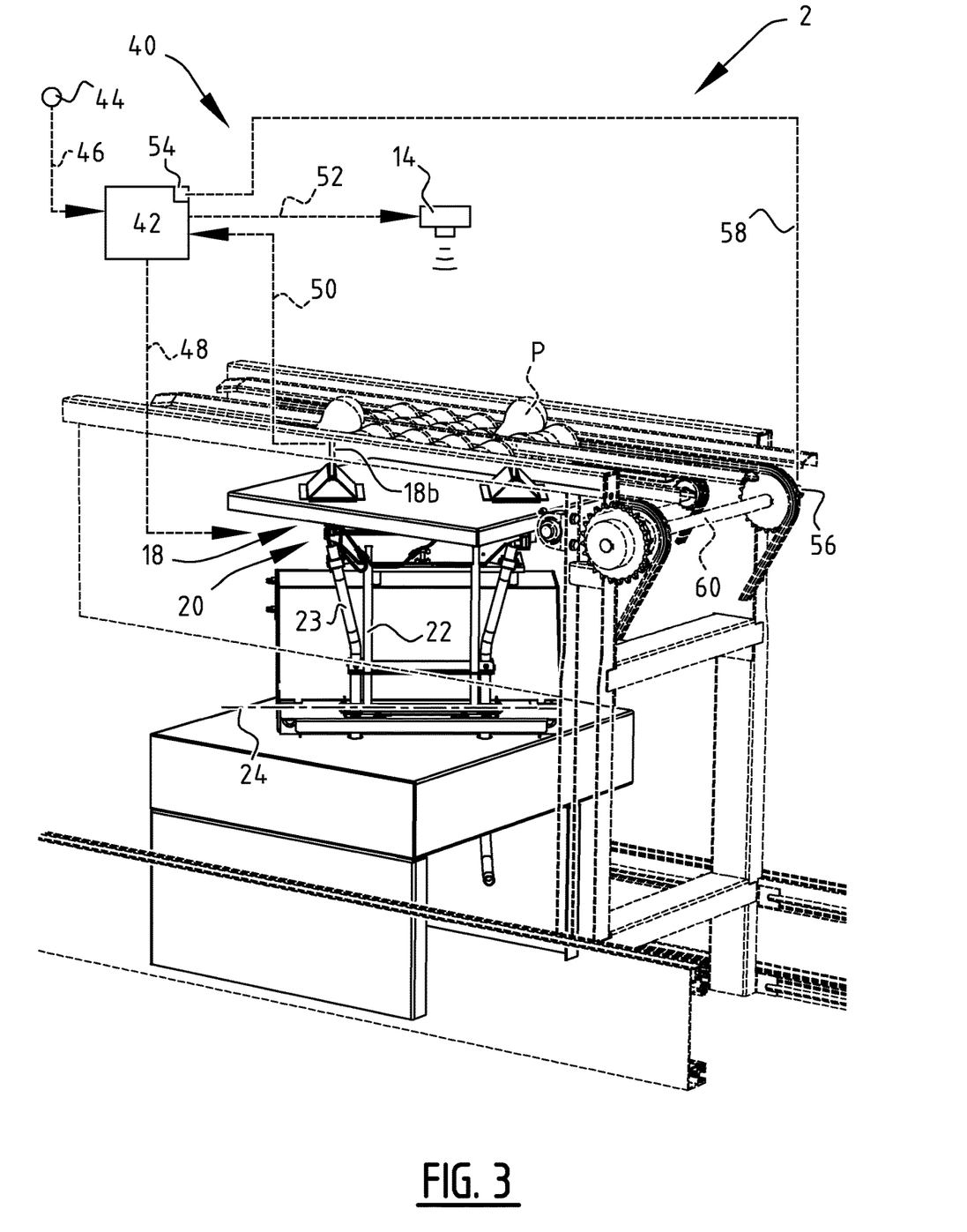
Figure 4:
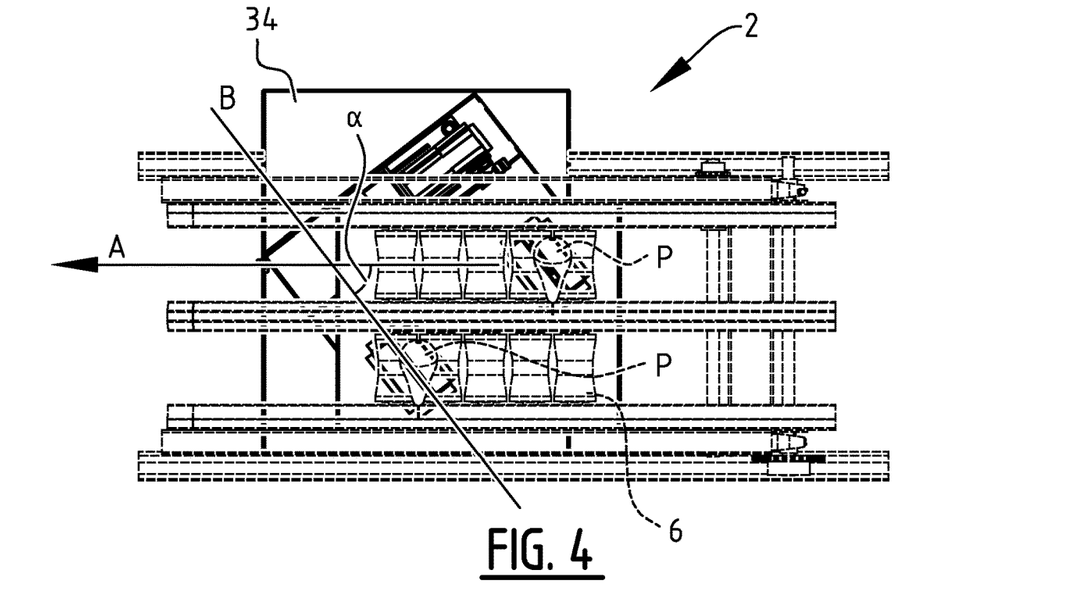
FIG. 4 shows a top view of the measuring device of FIGS. 1-3.
Figure 5:
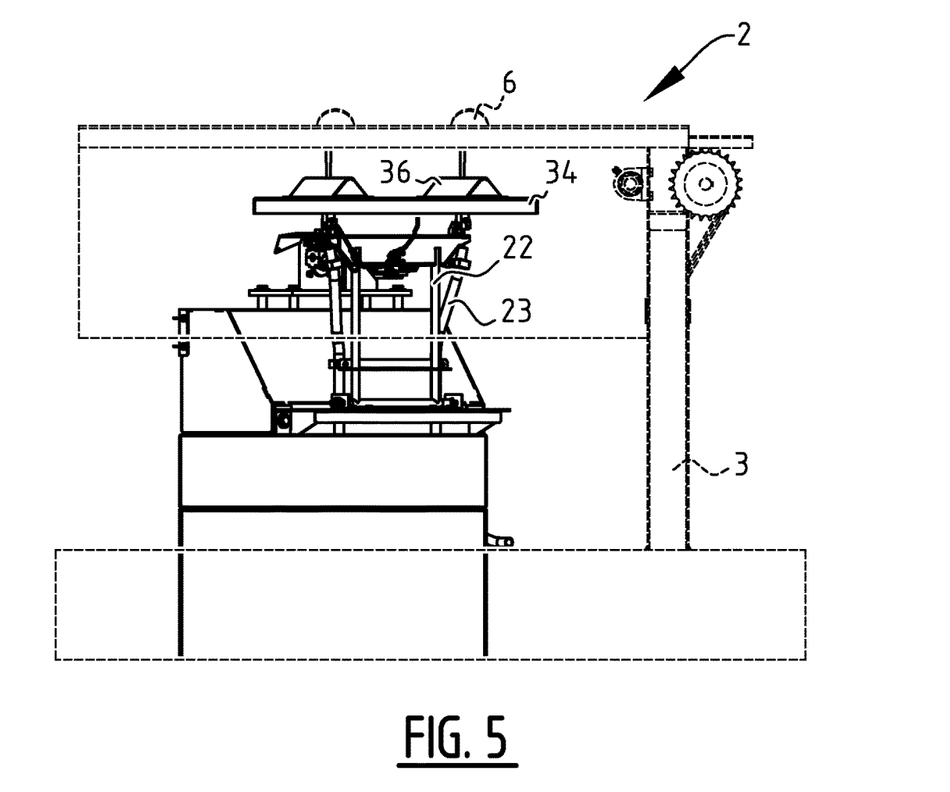
FIG. 5 shows a side view of the measuring device of FIG. 4.
Figure 6:
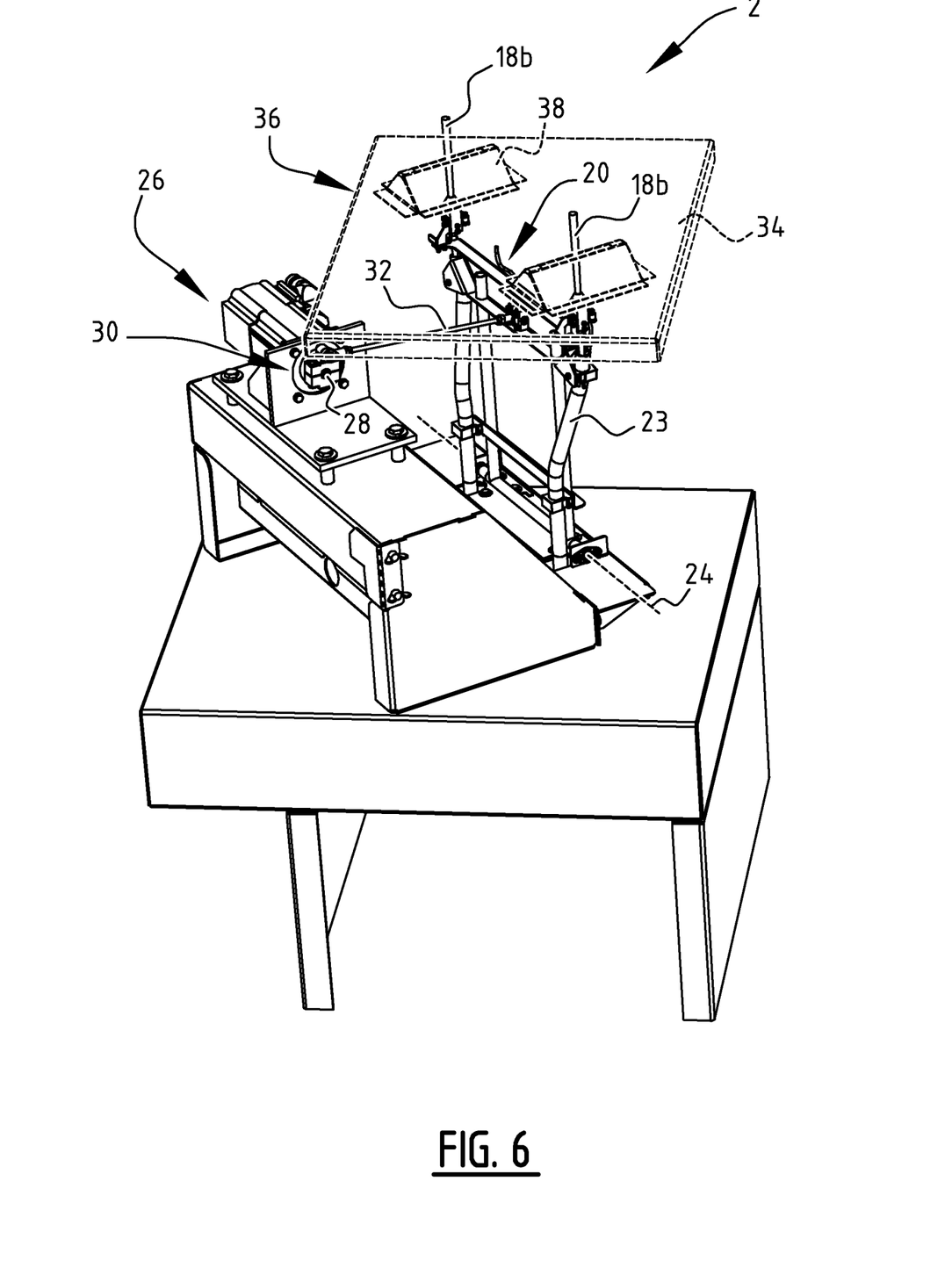
FIG. 6 shows a further view of the measuring device according to the invention.

Measuring device 2 (FIGS. 1-6) is provided with transport system 4 with diabolos 6.

In the shown embodiment rotation axis 24 is situated about 50 cm from the underside of diabolos 6. Measuring device 2 is further provided with frame 3 comprising transport system 4. In the shown embodiment transport system 4 is provided with first track 8 and second track 10. Products P, carried by diabolos 6, are movable in transport direction A. In the shown embodiment products P are pears. Measurements on singulated products P are performed using sensor/sensor system 12. Sensor system 12 comprises transmitter or signal source 14 arranged on the upper side of measuring device 2 and configured to transmit signal 16. On the lower side of fruit carriers 6 a number of receivers 18 is provided on arm 20 and configured to receive information beam 18b, which is shown schematically in the figures.

In the shown embodiment arm 20 can be moved by means of connecting arm 22 around rotation axis 24 using drive 26. In the shown embodiment flexible hose 23 is arranged for the measuring cable. In the shown embodiment rotation axis 24 is situated about 50 cm from the underside of diabolos 6. In the shown embodiment drive 26 is also provided with drive shaft 28, with which drive rod 32 can be moved using eccentric 30 such that arm 20 moves.

In the shown embodiment shielding plate 34 is provided with two recesses 36 corresponding to tracks 8, 10. Side shields 38 are provided here on either side of recess 36 for further shielding from disruptive influences.

Recess 36 extends in longitudinal direction B. In the shown embodiment longitudinal direction B and transport direction A form an angle α with each other. In the shown embodiment angle α is about 45°. It will be apparent that other angles, particularly in the range of 30° to 60°, are also possible.

Although in the shown embodiment arm 20 is movable around rotation axis 24, alternative embodiments are also possible. Arm 20 can thus be displaced linearly. It is also possible to position arm 20 fixedly relative to recess 36 and to provide a static receiver 18 or row of receivers 18.

Control system 40 (FIG. 3) comprises controller 42 which optionally receives detection signal 46 from product detector 44. Controller 42 then sends activation signal 48 to drive 26 in order to start the product measurement. Measuring signal 50, received from receivers 18, is then in the shown embodiment processed by controller 42. Controller 42 then preferably provides a quantitative value for the measured quality feature or quality features of product P. These quantitative values are then preferably used in the classification of products P for the purpose of sorting. In the shown embodiment controller 42 also controls transmitter 14 using control signal 52. It will be apparent that control system 40 can have central controller 42 and/or a number of local controllers.

In the shown embodiment controller 42 is provided with compensator 54, with which control signal 48 is adjusted on the basis of information 58 from encoder 56. Drive 26 is provided with information about the position of the transport unit by means of control signal 48. Drive 26 follows this signal over the position, such that during the outward movement receiver 18 follows the fruit on the transport system with a substantially linear movement throughout the measuring path, after which an accelerated return movement is made possible, such that the sensor is able to follow the next fruit. Drive 26 preferably comprises for this purpose a servomotor with its own control circuit and provided with its own position encoder on drive shaft 28. It is hereby possible to provide a substantially linear movement of arm 20 parallel to recess 36.

For the purpose of measuring product P, particularly a specific quality feature thereof, in the shown embodiment a product is detected using detector 44 and detection signal 46 is sent to controller 42. If product P has to be measured, activation signal 48 will be sent to drive 26 and control signal 52 to the one or more transmitters 14 of sensor system 12. In the currently preferred embodiment starting of drive 26 moves the one or more receivers 18 on arm 20 in coordination with the movement of product P by rotation around rotation axis 24. The signal which was originally transmitted by one or more transmitters 14, and is transmitted/radiated through product P, is then received here via recess 36 and along shield 34 by receiver(s) 18. The signal 50 received by receiver(s) 18 is then fed back to controller 42, which then performs an optional further processing on the measuring signal. In the shown embodiment measuring signal 50 is preferably converted into a quantitative indication of the relevant quality feature or features of product P. This information is then used for further sorting of products P.

In the shown embodiment a moving receiver 18 is shown in a two-track embodiment. It will be apparent that application is also possible in embodiments with a different number of tracks, for instance one, three or four. It is further possible to provide receiver 18 in an elongate embodiment, optionally with a row of static/fixed receivers 18. This enables a simplified embodiment in respect of coordination of relative movement according to the invention.

A number of further optional aspects of measuring device 2 is described in NL 1019600, including application of carriers in the form of grippers or cups, application of a lens system and/or mirrors.

The present invention is by no means limited to the above described preferred embodiments thereof. The rights sought are defined by the following claims, within the scope of which many modifications can be envisaged.

The invention claimed is:

1. A measuring device for measuring products, comprising:
    a frame provided with a number of movable fruit carriers on which or between which products can be placed for carrying and with which the products can be moved in a transport direction; and
    a sensor configured to perform a measurement or series of measurements on the products on or between the fruit carriers, wherein at least parts of the sensor are configured to enable the sensor to perform measurements over a measuring path, and wherein the measuring path is arranged at an angle to the transport direction so that a measurement can be performed over a distance over the product, wherein the angle lies in the range of 20 to 70 degrees to the transport direction.

2. The measuring device of claim 1, wherein the angle further lies in the range of 30 to 60 degrees to the transport direction.

3. The measuring device of claim 1, further comprising a shield arranged between the fruit carriers and at least parts of the sensor, wherein the shield is provided with an elongate recess substantially parallel to the measuring path, and wherein the elongate recess is configured for passage of a measuring signal.

4. The measuring device of claim 3, further comprising a moving device configured to move the sensor or parts thereof.

5. The measuring device of claim 4, wherein the moving device comprises a drive provided with an arm on which the sensor or parts thereof are arranged, and wherein the arm is provided for rotation around a rotation axis.

6. The measuring device of claim 5, wherein the drive is provided with a compensator configured to compensate for the movement of the arm such that a linear movement of the sensor running substantially synchronously with the transport system can be realized while the measurement is being performed.

7. The measuring device of claim 1, further comprising a moving device configured to move the sensor or parts thereof.

8. The measuring device of claim 7, wherein the moving device comprises a drive provided with an arm on which the sensor or parts thereof are arranged.

9. The measuring device of claim 8, wherein the arm is provided for rotation around a rotation axis.

10. The measuring device of claim 9, wherein the drive is provided with a compensator configured to compensate for the movement of the arm such that a linear movement of the sensor running substantially synchronously with the transport system can be realized while the measurement is being performed.

11. The measuring device of claim 8, wherein the drive is provided with a compensator configured to compensate for the movement of the arm such that a linear movement of the sensor running substantially synchronously with the transport system can be realized while the measurement is being performed.

12. The measuring device of claim 1, wherein the measuring device further comprises a controller which is operatively connected to the sensor and is configured to control the measurement on the basis of a product detection.

13. The measuring device of claim 1, wherein the sensor is provided on the lower side of the fruit carriers on which or between which the products can be carried.

14. The measuring device of claim 1, wherein the sensor comprises one or more signal receivers and the measuring device is further provided with one or more signal transmitters.

15. The measuring device of claim 1, wherein the sensor processes signals with different frequencies or frequency spectra in succession.

16. The measuring device of claim 1, wherein the sensor comprises one or more of a physical hardness tester, laser, methane sensor, ultrasonic sensor, spectrometer, X-ray detector, and photosensitive element.

17. The measuring device of claim 1, wherein the fruit carriers comprise diabolos.

18. A sorting system provided with the measuring device of claim 1.

19. A method for measuring products, the method comprising:
    providing a measuring device comprising:
        a frame provided with a number of movable fruit carriers on which or between which products can be placed for carrying and with which the products can be moved in a transport direction, and
        a sensor configured to perform a measurement or series of measurements on the products on or between the fruit carriers, wherein at least parts of the sensor are configured to enable the sensor to perform measurements over a measuring path, and wherein the measuring path is arranged at an angle to the transport direction so that a measurement can be performed over a distance over the product;
    arranging a number of products on or between the fruit carriers;
    activating the sensor; and
    measuring the product over the measuring path at an angle that lies in the range of 20 to 70 degrees to the transport direction.

20. The method of claim 19, further comprising moving the sensor or parts thereof at an angle to the transport direction.

* * * * *